United States Patent
Kohls

(10) Patent No.: US 7,184,921 B2
(45) Date of Patent: Feb. 27, 2007

(54) PRINTED DIGITAL ECG SYSTEM AND METHOD

(75) Inventor: Mark Robert Kohls, New Berlin, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 0 days.

(21) Appl. No.: 10/716,285

(22) Filed: Nov. 18, 2003

(65) Prior Publication Data
US 2005/0107978 A1    May 19, 2005

(51) Int. Cl.
*G01D 1/00* (2006.01)
(52) U.S. Cl. ....................................... 702/127
(58) Field of Classification Search ............... 702/57, 702/66, 67, 127; 600/372, 373, 377, 382 600/300, 301
See application file for complete search history.

(56) References Cited

U.S. PATENT DOCUMENTS

| | | | |
|---|---|---|---|
| 6,459,264 B1 * | 10/2002 | Fain et al. .................. | 324/307 |
| 6,520,910 B1 * | 2/2003 | Kohls ......................... | 600/300 |
| 6,704,602 B2 * | 3/2004 | Berg et al. .................. | 607/60 |
| 6,748,256 B2 * | 6/2004 | Brodnick et al. ........... | 600/382 |
| 2003/0144699 A1 * | 7/2003 | Freeman ...................... | 607/5 |
| 2004/0138557 A1 * | 7/2004 | Le et al. ..................... | 600/428 |
| 2004/0186357 A1 * | 9/2004 | Soderberg et al. .......... | 600/300 |

FOREIGN PATENT DOCUMENTS

DE    101 50 364    *  4/2002

OTHER PUBLICATIONS

Translation of DE 101 50 364, Kohls, Apr. 2002.*

* cited by examiner

*Primary Examiner*—Michael Nghiem
(74) *Attorney, Agent, or Firm*—Fletcher Yoder

(57) ABSTRACT

A technique is provided for encoding physiological data, such as a digital ECG, as a set of high-resolution symbols. The set of high-resolution symbols may be printed on a printout of the physiological data or other suitable medium. The set of high-resolution symbols may scanned, or otherwise acquired, and decoded to reconstruct all or a portion of the original set of physiological data.

30 Claims, 2 Drawing Sheets

PRINTED DIGITAL ECG SYSTEM AND METHOD

BACKGROUND OF THE INVENTION

The present invention relates generally to the field of medical monitoring and more specifically to the field of storage of data, such as waveforms or other physiological data representations, acquired during medical monitoring or diagnostic testing. In particular, the present invention relates to the generation of a set of high-resolution characters representative of a set of physiological data and to the reconstruction of a set of physiological data from such a set of high-resolution characters.

Electrocardiograph (ECG) systems measure cardiac electrical activity associated with the muscular pumping activity of the heart. The electrical activity is measured by contacts or leads placed on the body of the patient. Typically, the measured electrical activity may then be printed out as an ECG waveform or trace for review by a doctor or diagnostician.

In hospitals, added functionality and workflow integration may be provided by digital ECG systems that acquire and store the ECG data in a digital format. The digital ECG data may be stored on various magnetic or optical devices, may be transmitted to one or more display stations remote from the patient, and may be printed once or numerous times from the stored record. The digital ECG data, therefore, provides a degree of flexibility, security, and reproducibility that may not be easily obtained from non-digital ECG system that produce only a paper record of the ECG waveform or trace.

Despite the benefits of digital ECG, certain vulnerabilities may be created for hospitals using the digital technology. For example, digital records may be accidentally deleted, corrupted, or destroyed. Similarly, the accessible nature of digital records may create security or privacy concerns in the absence of a suitable controlled access implementation. Furthermore, paper savings, i.e., paperless ECG, may not be realized due to advantages of paper printouts, such as superior resolution, ease of side-by-side comparison, convenience, and so forth. As a result, even in hospitals utilizing digital ECG, the actual implementation may be a combination of digital acquisition and storage with analog printouts remaining the primary presentation of the ECG data to the physician.

Furthermore, outside of the hospital setting, digital ECG is not widespread, with paper ECG printouts remaining the primary or only record of a set of ECG data. For example, ECG data may be collected during physical exams or clinical testing, such as at doctor's offices, universities, clinics, and so forth, where the workflow or limited nature of the facility does not justify the use of a digital ECG system. As a result, the ECG data collected may never be converted into a digital format or entered into a database or other shared or archival system. Furthermore, the paper ECG printout may be lost, damaged, or destroyed with no way to recover or replace the ECG data acquired at that point in time. The present may be directed to one or more of the problems set forth above.

BRIEF DESCRIPTION OF THE INVENTION

The present technique provides a novel method and apparatus for storing and retrieving physiological data, such as digital ECG waveforms. The technique provides for the acquisition of a set of physiological data. A set of high-resolution symbols may be generated from the set of physiological data. The set of high-resolution symbols may be printed on a suitable medium, such as part of a printout of the set of physiological data. In addition, the technique provides for reconstructing all or part of the original set of physiological data from the set of high-resolution symbols. The reconstructed physiological data may be stored or printed for future reference.

In accordance with one aspect of the present technique, a method for storing physiological data is provided. A set of physiological data representative of one or more physiological parameters of interest is acquired. A set of high-resolution symbols from the set of physiological data may be generated and the high resolution symbols printed.

In accordance with a second aspect of the present technique, a method for acquiring a set of physiological data is provided. A set of high-resolution symbols is acquired from a printed medium. The set of high-resolution symbols is converted to a set of physiological data representative of one or more physiological parameters of interest. Systems and computer programs that afford functionality of the type defined by these methods are also provided by the present technique.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

The present technique may be used in conjunction with any application in which data is customarily printed and where digital storage or transfer techniques are unavailable or impractical. For example, different types of equipment used to measure various physiological parameters may generate paper reports or printouts of the measured physiological data, in which the physiological data set is represented as waveforms, traces, or arbitrary numbers. Examples of these types of systems include pulse oximeters, blood pressure monitors, defibrillators, electrocardiographs, and so forth. To the extent that the printout or report is the only record of the physiological events measured at that time, it may be difficult or impossible to provide the analog physiological data contained in the report to a centralized digital system, such as a database, for storage and retrieval. However, it may be desirable to have a digital record of the physiological data contained in the printout, particularly, where the physiological data forms part of a medical or clinical history, such as for doctor or hospital records or for pharmaceutical testing.

Accordingly, the present technique provides a mechanism by which physiological or other data may be provided on a printout or other printed medium in a digitized format. The digitized format may be used to subsequently reconstruct the data or provide the data to a database or other digital system. To simplify explanation, the present technique will be discussed in the context of a digital electrocardiograph (ECG) system. However, as one of ordinary skill in the art will appreciate, the present technique may be applied to other systems that customarily print an analog data set, such as monitoring systems for different physiological parameters and so forth.

Figure 1:
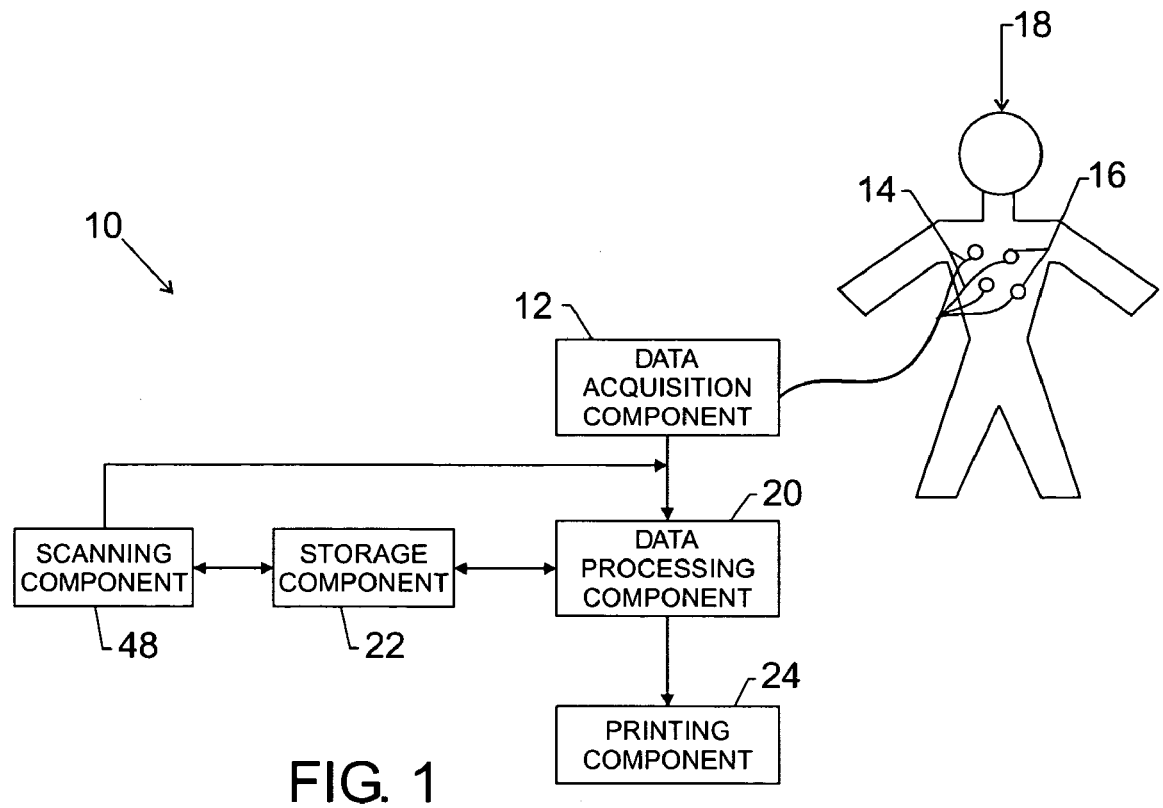
FIG. 1 is a diagrammatical view of an exemplary monitoring system in the form of an electrocardiograph for use in monitoring cardiac electrical activity, in accordance with one aspect of the present technique.

Turning now to the example of an ECG system, FIG. 1 depicts an exemplary ECG system 10 which may be used in conjunction with the present technique. The ECG system 10 may include a variety of components. For example, the ECG system 10 may include a data acquisition component 12 configured to receive electrical signals that convey the electrical activity of the heart, such as the polarization and depolarization events associated with cardiac contraction. The electrical signals may be conducted to the data acquisition component 12 via electrical leads 14 terminating in contact pads 16 which are positioned on the torso of the patient 18. While four leads 14 and contact pads 16 are depicted in FIG. 1 for simplicity, other numbers of leads 14 and contact pads 16 may be employed. In particular, twelve lead ECG systems 10 are frequently employed in cardiac monitoring.

The ECG system 10 may also include a data processing component 20 configured to receive and/or process the electrical signals. For example, the data processing component 20 may convert analog electrical signals to digital data, may analyze the data for recurring events or for events outside of a configured threshold, and/or may process the data for visual display, such as in a waveform, chart, graph, or text presentation. In this manner, the data processing component 20 may produce secondary data, such as timing, rhythm, alert events, variance, averages, and so forth, which may be useful. Similarly, the data processing component 20 may convert the ECG data into formats suitable for storage and/or display.

The processed ECG data may be transmitted to a storage component 22, such as one or more memory chips, magnetic drives, optical drives, and so forth, for short or long-term storage. The storage component 22 may be local or remote from the data processing component 22 and/or data acquisition component 12. For example, the storage component 22 may be a memory or storage device located on a computer network that is in communication with the data processing component 20. In the present context, the storage component 22 may also store programs and routines executed by the data processing component 20, including routines for implementing the present technique.

In addition, the data processing component 20 may transmit the processed ECG data to a printing component 24 for printing as an ECG printout or report. In general, the ECG printout may depict one or more waveforms representing all or part of the processed ECG data. For example, the ECG printout may successively depict only two to three seconds of the ECG data derived from each of the various leads 14 as a respective series of waveforms so that a reviewing doctor may evaluate the overall ECG data set at a glance. In addition, the ECG printout may contain patient and clinical data, such as name, date, procedure, doctor, and so forth, as well as secondary or derived data, such as heart rate and respective intervals for the cardiac phases.

Figure 2:
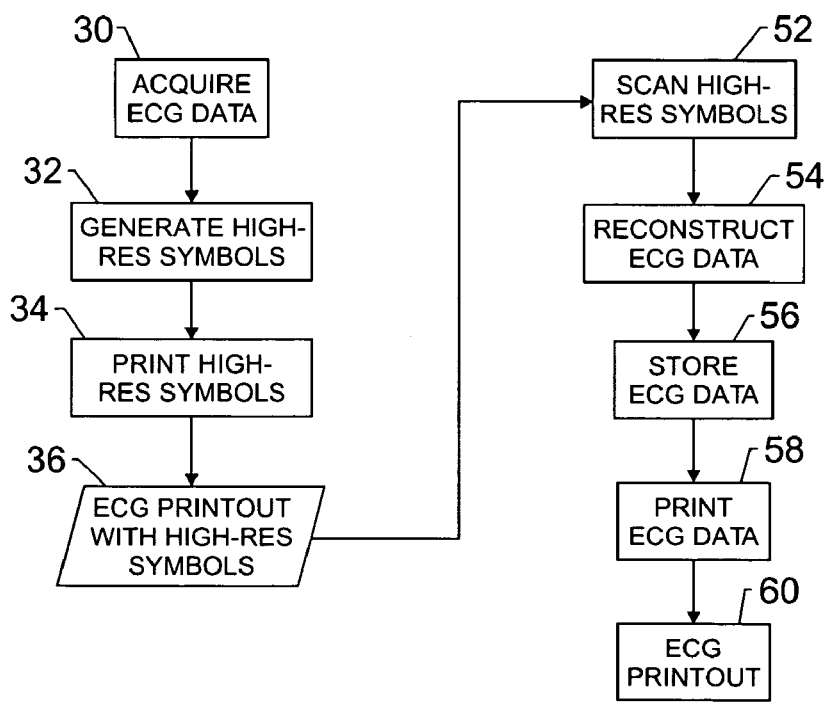
FIG. 2 is a flowchart depicting the technique of generating a set of high-resolution symbols from physiological data and of reconstructing all or part of the physiological data from the set of high-resolution symbols, in accordance with one aspect of the present technique.

The present technique utilizes the aforementioned components of an ECG system 10 in a novel manner to allow the storage and retrieval of the ECG data in a digital form on a printed medium. With reference now to FIG. 2, a flowchart is depicted which further illustrates the present technique. ECG data may be acquired, as depicted at step 30, such as by the data acquisition component 12, leads 14, and contacts 16 of an ECG system 10.

Figure 3:
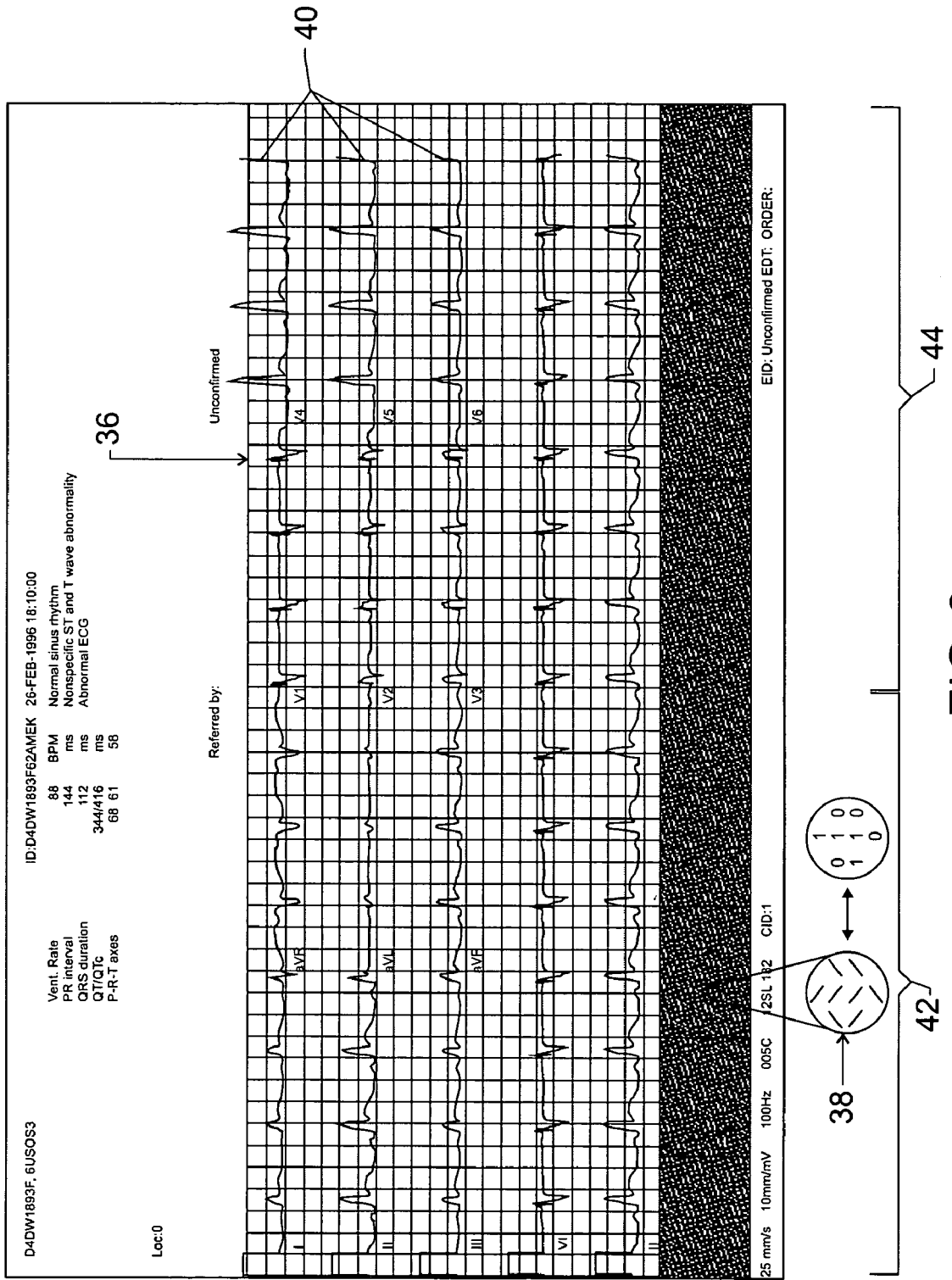
FIG. 3 is an exemplary ECG printout incorporating a set of high-resolution symbols representative of the accompanying digital ECG data.

The acquired ECG data may be used to generate respective high-resolution symbols, as depicted at step 32, which represent the acquired or processed ECG data in a digital, i.e., binary, format. The high-resolution symbols may be printed with the ECG data on an ECG printout 36, as depicted at step 34. An example of such an ECG printout 36 using high-resolution symbols 38 is depicted in FIG. 3. In the depicted ECG printout 36, the high-resolution symbols 38 are printed at high-density along the bottom of the printout 36. Alternatively, the high-resolution symbols 38 may be printed on a separate page of the printout 36, on the back of the printout 36, or on a separate page and/or report.

The high-resolution symbols 38 may consist of various character sets which may be distinguished at high-density and high-resolution and which may be used to convey binary information. Various high-density, high-resolution printing and/or two-dimensional barcoding schemes may be employed in selecting a set of high-resolution symbols 38. In addition factors such as the desired information density, i.e., bytes, per square inch of print and/or the desired vertical and horizontal print resolutions may be considered in selecting a set of high-resolution symbols 38 or a printing scheme.

In the example of FIG. 3, forward slashes (/) and backward slashes (\) are depicted as the high-resolution symbols 38 which respectively equate to 0 and 1, i.e., binary data. The respective ECG waveforms 40 may, therefore, be encoded as binary data in the form of the high-density, high-resolution symbols 38 contained on the printout 36. Similarly, other information that may or may not otherwise appear on the printout, such as patient information, derived parameters, clinic information, procedure information, and so forth, may be encoded by the high-resolution symbols 38.

Furthermore, an increased or reduced amount of ECG data, relative to the ECG waveforms 40 printed on the ECG printout 36, may be encoded via the high-resolution symbols 38. For example, though the printed ECG waveforms 40 may only convey a reduced portion of the total acquired ECG information, such as two to three seconds of information for each lead 14, a larger portion or all of the ECG data may be encoded and printed as high-resolution symbols 38 at high-density. Alternatively, only that ECG data which is present on the printout 36 as a waveform 40 may be encoded on the printout 36 as high-resolution symbols 38. Similarly, less of the ECG data may be encoded than is displayed as waveforms 40. For example, encoding a smaller subset of the ECG data may be desirable when the encoded data is desired primarily as a reference or when ECG data indicative of problems or irregularities is of primary interest.

To provide data integrity, the encoded ECG data may be repeated at regular or irregular intervals to provide the desired degree of data redundancy. Similarly, indicators of data completeness, such as checksum or cyclic redundancy check (CRC) values, may be included with the encoded ECG data which may be used to verify the integrity of the data set. For example, referring once again to FIG. 3, a first region 42 containing the high-resolution symbols 38 may represent a first instance of the encoded data. A second region 44 may represent a second instance of the encoded data, either in a fully or partially redundant form. In this manner, damage or destruction of a portion of the printout 36 containing the high-resolution symbols 38 will not necessarily result in a non-functional or non-retrievable set of encoded data. As one of ordinary skill in the art will appreciate, the desired degree of redundancy may reflect the importance or irreplaceability of the ECG data.

The retrieval or reading of the ECG data encoded by the high-resolution symbols 38 may be accomplished in a variety of manners. For example, if the ECG system 10 includes a scanning component 48 (FIG. 1), the high-resolution symbols 38 may be read by the scanning component 48, as depicted at step 52 of FIG. 2. High-resolution symbols 38 acquired in this manner may be stored temporarily, such as at storage component 22, or may be reconstructed by the data processing component 20 to generate the original ECG data encoded by the high-resolution symbols 38, as depicted at step 54 of FIG. 2. Once reconstructed, the ECG data may be stored, such as at the storage component 22, as depicted at step 56 of FIG. 2. The reconstructed ECG data may also be printed by the printing component 24, as depicted at step 58. The printing component 24 may retrieve the ECG data from the data processing component 20 or the storage component 22. The resulting second ECG printout 60 may or may not contain high-resolution symbols 58 encoding the ECG data. In addition, the second ECG printout 60 may depict all or a portion of the reconstructed ECG data.

In this manner, the ECG printout 36 commonly used by doctors and other medical personnel may be used to digitally store and reproduce the ECG data. In particular, ECG data obtained by systems that are not connected to a database or storage system may be digitally stored and shared by encoding the ECG data on ECG printouts 36 using the high-resolution symbols 38. In this manner, ECG data obtained during clinical or pharmaceutical trials or at a doctor's office may be digitally stored and subsequently accessed via scanning the high-resolution symbols 38 and reconstructing the ECG data. Furthermore, interpretation and/or reconstruction of the high-resolution symbols 38 would typically be accomplished by a properly configured ECG system 10. As a result, a printout containing ECG data encoded as high-resolution symbols 38 may be publicly accessible or viewable without substantial risk that the encoded patient information would be intelligible to a third party, or even the patient.

Though the present discussion focuses on an implementation in the field of ECG, other monitoring modalities which typically produce a written document may benefit from the present technique. For example, in the field of medical monitoring, the present technique may be implemented not only in ECG, but also with pulse oximetry, electroencephalography (EEG), defibrillation monitors, and so forth. In general, the present technique may be employed with any data, physiological or otherwise, that is customarily printed.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A physiological monitoring system, comprising:
   a data acquisition component configured to acquire a set of physiological data;
   a data processing component configured to generate a first representation of the set of physiological data in a first format, and to generate a second representation of the set of physiological data in a second format including at least partial redundancy of the set of physiological data, wherein the second format is a binary format; and
   a printing component configured to print at least the second representation onto a suitable medium in the binary format.

2. The physiological monitoring system as recited in claim 1, wherein the set of physiological data comprises a set of electrocardiograph (ECG) data.

3. The physiological monitoring system as recited in claim 1, wherein the printing component is configured to print the first and second representations.

4. The physiological monitoring system as recited in claim 1, further comprising two or more sensor leads connected to the data acquisition component via respective lead wires.

5. The physiological monitoring system as recited in claim 1, further comprising a storage component configured to receive at least one of the first representation or the second representation.

6. The physiological monitoring system as recited in claim 1, further comprising a scanning component configured to read at least one of the first representation or the second representation from the suitable medium.

7. The physiological monitoring system as recited in claim 6, wherein the data processing component is configured to reconstruct the first representation from the second representation.

8. The physiological monitoring system as recited in claim 7, wherein the printing component is configured to print the first representation onto a printout.

9. The system as recited in claim 1, wherein the data processing component is configured to generate a plurality of binary symbols digitally encoding the set of physiological data.

10. The system as recited in claim 1, wherein the first format is an analog format.

11. The system as recited in claim 10, wherein the analog format comprises at least one of a waveform, a chart, or a graph.

12. The system as recited in claim 10, wherein the second format comprises a binary encoding of the set of physiological data.

13. The system as recited in claim 10, wherein the second format includes at least one of error detection or error correction information.

14. The system as recited in claim 13, wherein the error detection comprises at least one of a check-sum or a cyclic redundancy check.

15. A method for storing physiological data, comprising:
   acquiring a set of physiological data representative of one or more physiological parameters of interest;
   generating a set of binary symbols from the set of physiological data, wherein the set of binary symbols digitally represents the set of physiological data and includes at least partial redundancy of the set of physiological data; and
   printing the binary symbols.

16. The method as recited in claim 15, wherein the set of physiological data comprise one or more digital electrocardiograph (ECG) waveforms.

17. The method as recited in claim 15, wherein the set of physiological data comprise one or more digital waveforms.

18. The method as recited in claim 15, wherein printing the binary symbols comprises printing the binary symbols onto a printout of at least a portion of the set of physiological data.

19. A computer program, provided on one or more computer readable media, for storing physiological data, comprising:
a routine for acquiring a set of physiological data representative of one or more physiological parameters of interest;
a routine for generating a set of binary symbols from the set of physiological data, wherein the set of binary symbols digitally represents the set of physiological data and includes at least partial redundancy of the set of physiological data; and
a routine for printing the binary symbols.

20. The computer program as recited in claim 19, wherein the set of physiological data comprises one or more digital electrocardiograph (ECG) waveforms.

21. A method for acquiring a set of physiological data, comprising:
acquiring a set of binary symbols from a printed medium with a device, wherein the set of binary symbols digitally represents and is at least partially redundant of a set of physiological data representative of one or more physiological parameters of interest;
extracting the set of physiological data from the set of binary symbols; and
outputting and/or storing the set of physiological data for use by a user.

22. The method as recited in claim 21, wherein the set of physiological data comprises one or more digital electrocardiograph (ECG) waveforms.

23. The method as recited in claim 21, further comprising storing the set of physiological data on a computer-accessible medium.

24. The method as recited in claim 21, further comprising printing at least a portion of the set of physiological data.

25. A computer program, provided on one or more computer readable media, for acquiring a set of physiological data, comprising:
a routine for acquiring a set of binary symbols from a printed medium, wherein the set of binary symbols digitally represents a set of physiological data representative of one or more physiological parameters of interest;
a routine for extracting the set of physiological data from the set of binary symbols; and
a routine for outputting and/or storing the set of physiological data for use by a user.

26. The computer program as recited in claim 25, wherein the set of physiological data comprises one or more digital electrocardiograph (ECG) waveforms.

27. The computer program as recited in claim 25, further comprising a routine for storing the set of physiological data on a computer-accessible medium.

28. The computer program as recited in claim 25, further comprising a routine for printing at least a portion of the set of physiological data.

29. An electrocardiograph (ECG) system, comprising:
means for acquiring a set of physiological data representative of one or more physiological parameters of interest;
means for generating a set of binary symbols from the set of physiological data, wherein the set of binary symbols digitally represents and is at least partially redundant of the set of physiological data; and
means for printing the binary symbols.

30. An electrocardiograph (ECG) system, comprising:
means for acquiring a set of binary symbols from a printed medium with a device, wherein the set of binary symbols digitally represents and is at least partially redundant of a set of physiological data representative of one or more physiological parameters of interest; and
means for extracting the set of physiological data from the set of binary symbols; and
means for outputting and/or storing the set of physiological data for use by a user.

* * * * *